(12) United States Patent
Gharda

(10) Patent No.: US 8,507,693 B2
(45) Date of Patent: Aug. 13, 2013

(54) PROCESS FOR SYNTHESIS OF FIPRONIL

(76) Inventor: Keki Hormusji Gharda, Mumbai (IN)

( * ) Notice: Subject to any disclaimer, the term of this patent is extended or adjusted under 35 U.S.C. 154(b) by 0 days.

(21) Appl. No.: 13/601,107

(22) Filed: Aug. 31, 2012

(65) Prior Publication Data

US 2013/0030190 A1  Jan. 31, 2013

Related U.S. Application Data

(63) Continuation of application No. PCT/IN2010/000496, filed on Jul. 28, 2010.

(30) Foreign Application Priority Data

Mar. 3, 2010  (IN) .......................... 552/MUM/2010

(51) Int. Cl.
*C07D 231/10* (2006.01)
(52) U.S. Cl.
USPC ...................................... 548/367.4
(58) Field of Classification Search
None
See application file for complete search history.

(56) References Cited

FOREIGN PATENT DOCUMENTS

| AU | 2010100312 A4 | 5/2010 |
|---|---|---|
| CN | 101289400 A | 10/2008 |
| EP | 0295117 A1 | 12/1988 |
| GB | 2154581 A | 9/1985 |
| WO | WO 00/35851 | 6/2000 |
| WO | WO 01/30760 A1 | 5/2001 |

OTHER PUBLICATIONS

Grant & Hackh's Chemical Dictionary (5th Ed. 1987) at p. 148.*
Hai-yun Zhao et al., "Research on the Synthesis Crafts of Fipronil," Modern Agrochemicals, vol. 7 No. 4, Aug. 2008, 14 pages.

* cited by examiner

*Primary Examiner* — Samantha Shterengarts
(74) *Attorney, Agent, or Firm* — Brinks Hofer Gilson & Lione

(57) ABSTRACT

The present disclosure relates to a process for trifluoromethylsulfinyl pyrazole compound of formula I, from a compound of formula III, wherein, R, $R_1$ and $R_2$ represent a group containing halogen group respectively and $R_3$ represents a perhaloalkyl.

17 Claims, No Drawings

PROCESS FOR SYNTHESIS OF FIPRONIL

RELATED FOREIGN APPLICATION DATA

The present application is a continuation application of PCT Application No. PCT/IN2010/000496, filed Jul. 28, 2010, which claims priority to Indian Patent Application No. 552/MUM/2010, filed Mar. 3, 2010, the entirety of both of which are hereby incorporated by reference.

FIELD

The present disclosure relates to a process for preparing trifluoromethylsulfinyl pyrazole derivatives.

Particularly, the present disclosure envisages a process for preparing 5-Amino-1-(2,6-dichloro-4-trifluoromethylphenyl)-3-cyano-4-trifluoromethyl sulfinyl pyrazole also known as Fipronil.

BACKGROUND AND PRIOR ART

5-Amino-1-(2,6-dichloro-4-trifluoromethylphenyl)-3-cyano-4-trifluoromethyl sulfinyl pyrazole or 5-Amino-[2,6-dichloro-4-(trifluoromethyl)phenyl]-4-[-(1(R,S)-trifluoromethyl)sulfinyl]-1H-pyrazole-3-carbonitrile also known as Fipronil is a novel pesticide characterized by high efficiency, low toxicity and especially low residue.

There are various routes to synthesize Fipronil by oxidation of thiopyrazole with various other oxidizing agents in suitable solvents. Oxidation of sulfides is a very useful route for the preparation of sulfoxides. Literature is replete with the conversion of sulfides to sulfoxides and/or sulfones. However, most of the existing methods use expensive, toxic or rare oxidizing reagents, which are difficult to prepare, are very expensive and cannot be used on commercial scale. Many of these processes suffer from poor selectivity.

WO01/30760 describes oxidation of 5-amino-1-(2,6-dichloro-4-trifluoromethylphenyl)-3-cyano-4-trifluoromethylthio-pyrazole with trifluoro-acetic acid and hydrogen peroxide in the presence of boric acid. The quantity of trifluoroacetic acid used is 14.5 molar equivalents. The patent also discloses the preparation of 5-amino-1-(2,6-dichloro-4-trifluoromethyl phenyl)-3-cyano-4-trifluoromethylthio-pyrazole from 5-amino-1-(2,6-dichloro-4-trifluoromethyl phenyl)-3-cyano pyrazole-4-yl disulphide.

European Patent publication No. 295117 describes the preparation of 5-amino-1-(2,6-dichloro-4-trifluoromethylphenyl)-3-cyano-4-trifluoromethylsulphinyl pyrazole starting from 2,6-Dichloro-4-trifluoromethylaniline to give an intermediate 5-amino-1-(2,6-dichloro-4-trifluoromethylphenyl)-3-cyano-4-trifluoromethylthiopyrazole which is oxidized with meta-chloroperbenzoic acid in chloroform to give desired product.

Oxidizing agents such as perbenzoic acids do not provide effective and regioselective oxidation of electron deficient sulfides such as trifluoromethylsulphides which are less readily oxidized than other sulfides. Trifluoroacetic acid and trichloroacetic acid are found to be very efficient and regioselective oxidation medium for oxidation of 5-amino-1-(2,6-dichloro-4-trifluoromethylphenyl)-3-cyano-4-trifluoromethylthio-pyrazole in presence of hydrogen peroxide. Trichloroacetic acid can not be used alone due to higher melting point. Trifluoroacetic acid on the other hand is very regioselective with respect to conversion and low by-products formation. However, it is expensive, water miscible, corrosive to metal as well as glass, comparatively lower boiling and it's recovery (in anhydrous form) is complex in nature.

WO00/35851/2000 talks about synthesis of 2,6-Dichloro-4-trifluoromethylaniline starting from 3,4,5-trichloro-benzotrifluoride in the presence of alkaline fluorides like lithium fluoride and ammonia in the presence of N-methylpyrrolidone at 250° C. to give 97% conversion and 87% selectivity. The main drawback of the above process is the synthesis of 3,4,5-trichlorobenzotrifluoride in high yield and purity. Chlorination of p-chlorobenzotrifluoride gives a mixture of 3,4,5-trichlorobenzotrifluoride in 72% GLC conversions, 3,4-dichloro and tetrachlorobenzotrifluoride. The process to get pure 3,4,5-isomer from this mixture by fractionation followed by crystallization is very tedious. Moreover in-spite of using very pure intermediates, substantial amount of an undesired isomer (3-amino-4,5-dichlorobenzotrifluoride) is also obtained.

Another approach to generate 3,4,5-trichlorobenzotrifluoride with high yield and purity is to perform denitrochlorination of 4-chloro-3,5-dinitrobenzotrifluoride in the presence of a catalyst as described in GB Patent 2154581A. Even though the process produces 3,4,5-trichlorobenzotrifluoide in high yield and purity, the reaction conditions are too drastic to be employed for an industrial process.

The known commercial processes for the manufacture of Fipronil uses corrosive and expensive chemical such as trifluoroaceticacid, hydrogen peroxide and m-chloroperbenzoicacid Trifluoroacetic acid is expensive and generally not used in large quantities, as well as of m-chloroperbenzoic acid is difficult to handle at commercial scale due to its un-stability and detonating effect. Also the raw material used such as 2,6-Dichloro-4-trifluoromethylaniline are not easily available or made. The overall process for the Fipronil as disclosed above is found to be unsatisfactory in one respect or the other.

Thus, there is felt a need for preparing Fipronil from easily available raw materials in a simple and economical manner at an industrial level, with high yields and purity.

Objects

Some of the objects of the present disclosure, which at least one embodiment herein satisfies, are as follows:

The main object of the present disclosure is to provide a convenient and economically feasible process for preparing trifluoromethylsulfinyl pyrazole compound.

Another object of the present disclosure is to provide a process for preparing Fipronil using easily and commercially available raw materials.

Yet, another object of the present disclosure is to provide a process for preparing Fipronil in high yield and high purity.

Other objects and advantages of the present disclosure will be more apparent from the following description which is not intended to limit the scope of the present disclosure.

SUMMARY

In accordance with the present disclosure there is provided a process for the preparation of a trifluoromethylsulfinylpyrazole compound of formula I,

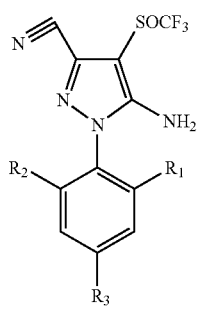

I said process comprising:
a) halogenating an aromatic compound of formula II:

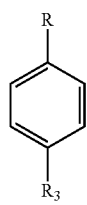

II wherein, R is a halogen and $R_3$ is a perhaloalkyl, to obtain a polyhalogenated perhaloalkyl benzene compound of formula III;

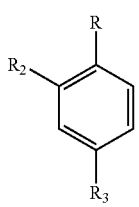

III wherein, R, $R_2$ contain elements of halogen group respectively; and $R_3$ is a perhaloalkyl,
b) reacting in a polar solvent selected from a group selected from a group consisting of N-methylpyrrolidone, dimethylsulfone, N,N'-dimethyl imidazolidinone and diphenylsulfone, preferably N-methylpyrrolidone; the compound of formula III with anhydrous ammonia in the presence of an alkali halide, preferably potassium fluoride; at a temperature of about 200° C. to 300° C., preferably in the range of 235° C. to 250° C.; and a pressure of about 20 kg/cm² to about 50 kg/cm², preferably in the range of 25 kg/cm² to about 42 kg/cm² to obtain a halo-perhaloalkyl aniline compound of formula IV;

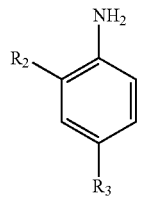

IV wherein R2 is halogen and R3 is a perhaloalkyl.
c) reacting halo-perhaloalkylaniline compound of formula IV with at least one halogenating agent selected from a group consisting of chlorine, sulfuryl chloride, thionyl chloride and phosphorus pentachloride; preferably sulfuryl chloride, in a chlorinated solvent selected from a group consisting of chloroform, dichloroethane, dichloromethane, chlorobenzene and o-dichlorobenzene to obtain a product mixture containing polyhalogenated perhaloalkylaniline compound of formula V;

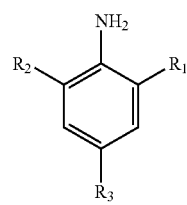

V wherein, R1 and R2 contain elements of halogen group respectively; and R3 is a perhaloalkyl;
d) isolating polyhalogenated perhaloalkylaniline compound of formula V from the product mixture, preferably by fractional distillation;
e) diazotizing the isolated polyhalogenated aniline compound of formula V with nitrosyl sulfuric acid in the presence of an acid solvent to form a diazotized derivative of compound V;
f) reacting the diazotized derivative of compound V with cyanoalkyl propionate derivative and ammonia at a temperature range of about 0° C. to 25° C. to obtain a reacted mixture containing pyrazole compound of formula VII;

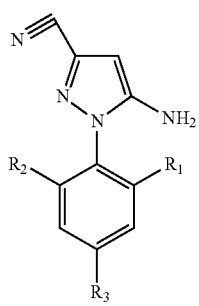

VII wherein, $R_1$ and $R_2$ contain elements of halogen group respectively; and $R_3$ is a perhaloalkyl;
g) isolating the pyrazole compound of formula VII from the reacted mixture with a halogenated aliphatic hydrocarbon solvent followed by evaporating the solvent to yield crude pyrazole compound VII;

h) sulfenylating the crude pyrazole compound VII with a sulfenylating agent preferably trifluoromethyl sulfenyl chloride in a halogenated aliphatic hydrocarbon solvent to obtain a product mixture containing thiopyrazole compound of formula IX.

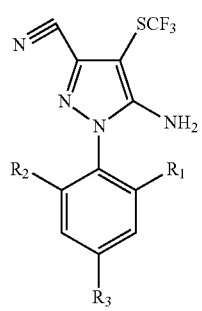

wherein, $R_1$ and $R_2$ contain elements of halogen group respectively; and $R_3$ is a perhaloalkyl; followed by isolating the thiopyrazole compound form the product mixture;

i) oxidizing the isolated thiopyrazole compound of formula IX at a temperature 10° C. to 30° C. in a reaction medium comprising an oxidizing agent which is a peroxide compound selected from the group consisting of hydrogen peroxide, tert-butyl hydrogen peroxide, benzoyl peroxide and sodium peroxide, preferably hydrogen peroxide; a solvent system comprising in various ratios at least two solvents selected from a group of halogenated solvents consisting of trichloroacetic acid, di chloroacetic acid, mono bromoacetic acid, di bromoacetic acid, tri bromoacetic acid, chlorobenzene, dichloromethane and dichloroethane; and a corrosion inhibitor, preferably boric acid, to yield a product mixture containing trifluoromethyl sulfinyl pyrazole compound of formula I; and j) optionally purifying trifluoromethyl sulfinyl pyrazole compound of formula I by at least one process selected from the process consisting of crystallization which is carried out using at least one solvent selected from a group consisting of toluene, chlorobenzene and ethyl acetate; and leaching which is carried out using at least one solvent selected from a group consisting of toluene, chlorobenzene and ethyl acetate; preferably a mixture of chlorobenzene and ethyl acetate.

In preferred embodiment of the present disclosure R, $R_1$ and $R_2$ are chlorine, and $R_3$ is trifluoromethyl.

In accordance with yet another aspect of the present disclosure the solvent system in oxidation step (i) is a mixture of trichloroacetic acid, dichloroacetic acid and chlorobenzene.

Typically, the chlorobenzene content in the mixture ranges from 20% to 30% w/w.

In accordance with another aspect of the present disclosure the solvent system in oxidation step (i) is a mixture of trichloroacetic acid and chlorobenzene in a ratio of 80:20% w/w.

Typically, trichloroacetic acid is used in the amount of 5 to 14 molar equivalents.

Typically, the amount of hydrogen peroxide used is about 0.5 moles to about 1.2 moles per mole of the compound of formula IX.

Typically, the compound of formula II is 4-chlorobenzotriflouride.

The compound of formula III is 3,4-dichlorobenzotriflouride.

The compound of formula IV is 2-chloro-4-trifluoromethylaniline.

The compound of formula V is 2,6-dichloro-4-trifluoromethylaniline.

The cyanoalkyl propionate derivative is ethyl-2,3-dicyanopropionate of formula VI.

The compound of formula VII is 5-amino-3-cyano-1-(2,6-dichloro-4-trifluoro methyl phenyl)-pyrazole.

The compound of formula IX is 5-amino-[2,6-dichloro-4-(trifluoromethyl)phenyl]-4-[trifluoromethylsulfenyl]-1H-pyrazole-3-carbonitrile.

Typically, the chlorobenzene content in the mixture used for leaching ranges from 5% to 100% v/v.

Typically, the chlorobenzene used for leaching is in the ratio 2 to 10 preferably in the ratio 3 to 4 parts per part of trifluoromethylsulfinyl pyrazole compound I.

In preferred embodiment of the present disclosure the trifluoromethyl sulfinyl pyrazole compound of formula I is 5-amino-[2,6-dichloro-4-(trifluoromethyl)phenyl]-4-[-(1-(R,S)-trifluoro methyl)sulfinyl]-1H-pyrazole-3-carbonitrile.

Typically, the purity of 5-amino-[2,6-dichloro-4-(trifluoromethyl)phenyl]-4-[-(1(R,S)-trifluoromethyl)sulfinyl]-1H-pyrazole-3-carbonitrile is greater than 98%.

DETAILED DESCRIPTION

The process for trifluoromethyl sulfinyl pyrazole compound of formula I is illustrated with reaction sequence as depicted below in scheme 1.

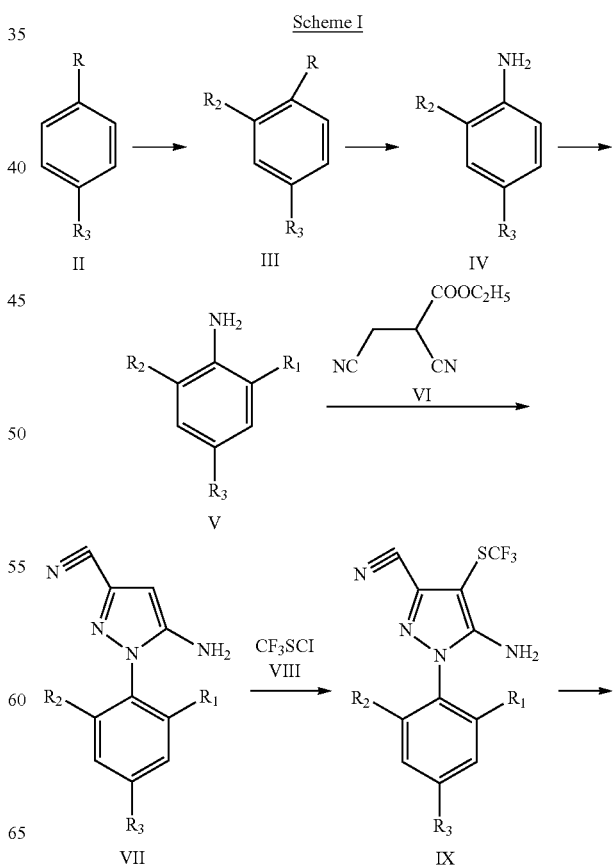

Scheme I

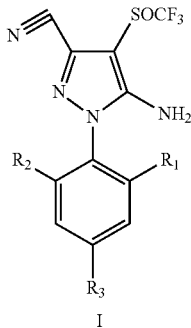

In accordance with the present disclosure polyhalogenated perhaloalkyl benzene compound of formula III is manufactured in high yields and purity by chlorination of aromatic compound of formula II. In preferred embodiment of the present disclosure compound II is p-chlorobenzotrifluoride.

Ammonolysis of polyhalogenated perhaloalkyl benzene compound of formula III to obtain halo-perhaloalkylaniline compound of formula IV is easier and facile as compared to that of p-chlorobenzotrifluoride (compound II) and much higher conversions as compared to that of p-chlorobenzotrifluoride.

Polyhalogenated perhaloalkyl benzene compound of formula III is ammonolyzed with anhydrous ammonia in the presence of a solvent. Ammonolysis is conducted in the presence of alkali halides under pressure at 20 to 50 kg/cm$^2$ and in a temperature range of about 200° C. to about 300° C. Catalytic amounts of copper compound may be used during ammonolysis. The alkali halide is preferably potassium fluoride. Anhydrous ammonia is used in excess of 2-6 m/m to start with. As the reaction proceeds, more ammonia is fed to maintain the reactor pressure and to minimize side reactions, which predominate at higher temperature due to lowering of ammonia concentrations.

In a preferred embodiment of the present disclosure, the solvent employed in the present process can be any solvent or a mixture of solvent, which do not decompose under the reaction conditions and is inert with respect to the reactants. Preferably the solvent used is a polar solvent. The polar solvent is selected from a group consisting of N-methylpyrrolidine, N,N'-dimethylimidazolidinone, diphenyl sulfone and dimethylsulfone. N-methylpyrrolidone is the solvent of choice as it does not interact with the reactants and at the same time it solubilizes potassium fluoride.

Halo-perhaloalkylaniline compound is further halogenated to polyhalogenated perhaloalkyl aniline compound of formula V, halogenation is carried out using at least one of the halogenating agents selected from the group consisting of chlorine, thionyl chloride, sulfuryl chloride and PCl$_5$ at temperatures ranging between 0° C. to 100° C., preferably 0° C. to 70° C. The preferred halogenating agent is sulfuryl chloride. Among various halogens, the preferred halogen is chlorine unless a specific halogen is desired. The amount of halogenating agent used is limited to 10 to 50% excess, relative to the stoichiometric amount, preferably about 10-20% excess of the stoichiometric amount. Preferably, halogenation is done in chlorinated hydrocarbon solvents. The preferred solvents are chloroform, dichloroethane, dichloromethane, chlorobenzene and o-dichlorobenzene.

In preferred embodiment of the present disclosure, the compound of formula V is 2,6-dichloro-4-trifluoromethylaniline. It is further purified by fractional distillation of the product post halogenation. Distilled product can be crystallized from a suitable solvent to achieve the desired quality.

2,6-Dichloro-4-trifluoromethylaniline is diazotized with nitrosyl sulfuric acid in acid solvent and then treated with ethyl cyanopropionate compound and ammonia at a temperature ranging from 0 to 25° C. to give pyrazole derivative of formula VII, the pyrazole compound is further extracted from the reaction mixture by using halogenated aliphatic hydrocarbon. The solvent is then removed to isolate crude pyrazole.

In a preferred embodiment of the present disclosure, cyanoalkyl propionate derivative is ethyl-2,3-dicyanopropionate.

Crude pyrazole of formula VII is sulfenylated with a sulfenylating agent to give thiopyrazole compound of formula IX, the reaction is carried out in halogenated aliphatic hydrocarbon solvent. Thiopyrazole compound is further isolated by the distillation of the solvent.

In preferred embodiment of the present disclosure the sulfenylating agent is trifluoromethyl sulfenyl chloride.

Thiopyrazole compound of formula IX is then oxidized to trifluoromethyl sulfinylpyrazole compound of formula I, the oxidation is carried out in medium containing a solvent and an oxidizing agent. The oxidizing agent is selected from a group consisting of hydrogen peroxide, tert-butyl hydrogen peroxide, benzoyl peroxide and sodium peroxide. Most preferred oxidizing agent is hydrogen peroxide. The oxidation is carried out in the presence of corrosion inhibitor such as boric acid. The amount of hydrogen peroxide used is about 0.5 moles to about 1.2 moles per mole of the compound of formula IX.

The solvent used for oxidation is a mixture of at least two solvents selected from a group consisting of trichloroacetic acid, monobromoacetic acid dibromoacetic acid, tribromoacetic acid, chlorobenzene, dichloromethane and dichloroethane.

In accordance with another aspect of the present disclosure the solvent system in oxidation step (i) is a mixture of trichloroacetic acid and chlorobenzene in a ratio of 80:20% w/w.

In accordance with one of the preferred embodiments of the present invention the solvent system comprises monobromoacetic acid, dibromoacetic acid or tribromoacetic acid and chlorobenzene in various ratios.

In accordance with another aspect of the present disclosure the solvent system in step (i) is a mixture of trichloroacetic acid, dichloroacetic acid and chlorobenzene in a ratio of 70:30-80:20% w/w.

Typically, trichloroacetic acid is used in the amount of 5 to 14 molar equivalents.

The quantity of peroxide used depends on required optimal conversion with minimum by-product formation such as sulfone derivative.

In preferred embodiment of the present disclosure compound of formula IX is 5-Amino-[2,6-dichloro-4-(trifluoromethyl)phenyl]-4-[-(-trifluoromethyl)sulfenyl]-1H-pyrazole-3-carbonitrile.

In preferred embodiment of the present disclosure compound of formula I is (5-Amino-[2,6-dichloro-4-(trifluoromethyl)phenyl]-4-[-(1(R,S)-trifluoromethyl)sulfinyl]-1H-pyrazole-3-carbonitrile).

Crude Fipronil (5-Amino-[2,6-dichloro-4-(trifluoromethyl)phenyl]-4-[-(1(R,S)-trifluoromethyl)sulfinyl]-1H-pyrazole-3-carbonitrile), formula I thus formed is isolated by removing the solvent.

Crude Fipronil is further purified by crystallization using at least one solvent selected from a group consisting of esters of aliphatic acids and halogenated aromatic hydrocarbons, mainly ethyl acetate and chlorobenzene. The solvent mixture is used depending upon the associated impurities present in fipronil. Crystallized fipronil is further subjected to leaching using a solvent and/or a mixture of solvents selected from chlorobenzene and ethyl acetate. The fipronil thus obtained after crystallization and leaching has the purity of above 98%.

The present disclosure is further illustrated with respect to the following examples which do not limit the scope of the present disclosure in any way.

In the examples m/m means one gram mole of product obtained from one gram mole of substrate input.

EXAMPLES

Example—1

N-methylpyrrolidone (1050 ml) was charged in an autoclave along with 102 g anhydrous activated potassium fluoride, 377 g 3,4-dichlorobenzotrifluoride was added. Ammonia (158 g) gas was passed in the reactor from the pressure pot at ambient temperature. The content of the reactor was heated to 245° C.-250° C. over a period of 2 hours to get reactor pressure of 30-32 kg/cm². Excess $NH_3$ was fed from the pressure pot to maintain the reactor pressure at 38-40 kg/cm² at 245-250° C. liquid temperature. Reaction mixture was maintained at 245-250° C. and at 38-40 kg/cm² pressure for further 8 hours. Reaction mixture was cooled to ambient temperature and $NH_3$ was vented and recovered. Reaction mixture was filtered and on fractionation gave 77% yield of 2-chloro-4-trifluoromethylaniline and 13% yield of 2-chloro-5-trifluoromethyl aniline based on consumed 3,4-dichlorobenzotrifluoride.

Example—2

N-methylpyrrolidone (815 ml) was charged in an autoclave along with 291 g 3,4-dichlorobenzotrifluoride and 118 g of calcined potassium fluoride. Pressure pot was fitted to the autoclave. Ammonia (213 g) gas was fed into a reactor. Ammonia (158 g) gas was passed into the reactor from the pressure pot at ambient temperature initially and then the mixture in the autoclave was gradually heated to 245-250° C. liquid temperature and further maintained at temperature 245-250° C. and pressure of 38-40 kg/cm² for 6 hours by feeding ammonia gas to maintain the desired reactor pressure. After fractionation the yield of 2-chloro-4-trifluoromethylaniline was 75.2% based on 3,4-dichlorobenzotrifluoride consumed.

Example 3

3,4-Dichlorobenzotrifluoride (75.4 g) was added to 210 ml of N-methylpyrrolidone along with 30.45 g of calcined potassium fluoride & 1.73 g cuprous chloride and 6 g ammonia in an autoclave. Reaction mixture was maintained at 235° C. and pressure of 25-26 kg/cm² for 6 hrs. After work up and fractionation the yield of 2-chloro-4-trifluoromethyl aniline was 64% based on 3,4-dichlorobenzotrifluoride consumed.

Example 4

3,4-Dichlorobenzotrifluoride (75.4 g) was added to 210 g of dimethylsulfone δ 30.45 g of calcined potassium fluoride in an autoclave. The ammonia gas (1 to 1.2 m/m) was passed at 30° C. The reaction mixture was maintained at 235° C. and pressure of 25-26 kg/cm for 6 hrs. After work up and fractionation the yield of 2-chloro-4-trifluoromethylaniline was 84% based on 3,4-dichlorobenzotrifluoride consumed.

Example 5

3,4-Dichlorobenzotrifluoride (75.4 g) was added to 210 ml of N,N'-dimethylimidazolidinone along with 30.45 g of calcined potassium fluoride in an autoclave. Ammonia gas (1 m/m) was passed and the resultant reaction mixture was heated to 235° C. to get a pressure of 19 kg/cm². Ammonia gas was further fed to maintain the pressure of the resultant mixture at 25-26 kg/cm² pressure for further 6 hrs at 235° C. After fractionation the yield of 2-chloro-4-trifluoromethyl aniline was 71.8% based on 3,4-dichlorobenzotrifluoride consumed.

Example 6

A mixture (301 g) of 2-chloro-4-trifluoromethylaniline, 2-chloro-5-trifluoromethylaniline and N-methylpyrrolidone (NMP) (1.06 m/m) was mixed with 500 ml chlorobenzene. Sulfuryl chloride (148.4 g) was added to the mixture at 55-60° C. over a period of 4 hours and the reaction mixture was maintained at 55-60° C. for 4 hours. Reaction medium on treatment and fractionation gave 0.84 m of 2,6-dichloro-4-trifluoromethylaniline, 95% yield on 2-chloro-4-trifluoromethyl aniline.

Example 7

A mixture (276 g) of 2-chloro-4-trifluoromethylaniline, 2-chloro-5-trifluoromethylaniline and NMP (0.73 m/m) was mixed with 500 ml chlorobenzene. Sulfuryl chloride (135 g) was added to the mixture at 55-60° C. liquid temperature over a period of 4 hours and the reaction temperature was maintained for further 2 hours. Additional 20.2. g of sulfuryl chloride was added for completion of reaction. Reaction medium on treatment and fractionation gave 2,6-dichloro-4-trifluoromethylaniline, in 94% yield on 2-chloro-4-trifluoromethylaniline.

Example 8

A mixture (740 g) containing 2-chloro-4-trifluoromethyaniline, 2-chloro-5-trifluoromethylaniline and NMP (0.686 m/m) was charged with 400 ml dichloroethane in to the reactor. It was then heated to 55° C. and reacted with 430 g of sulfuryl chloride at 55-60° C. over a period of 4 hrs & further maintained at 65-70° C. for 2 hrs. The reaction mixture was worked up by adding water & treating with 5N NaOH, the organic layer was fractionated under reduced pressure to get 504.9 g of distilled 2,6-dichloro-4-trifluoromethylaniline. The yield of 2,6-dichloro-4-trifluoromethyl aniline was 93.5% on 2-chloro-4-trifluoromethylaniline.

Example 9

A mixture (270 g) containing 2-chloro-4-trifluoromethyl aniline, 2-chloro-5-trifluoromethylaniline and NMP (0.676 m/m) was mixed with 210 ml chlorobenzene. It was chlorinated by passing 1.22 m chlorine gas at 50-55° C. over a period of 8 hrs. The reaction mixture was worked up by adding water, treating the organic layer with 5N NaOH and the organic layer was fractionated under reduced pressure to get 92.5 g distilled 2,6-dichloro-4-trifluoromethylaniline.

Example 10

Sodium 38.6 g was dissolved in ethanol 500 ml. The obtained sodium ethoxide solution was added to 201 g of ethyl cyanoacetate over 0.5 hour to get a slurry of sodium salt of ethyl cyanoacetate. The above slurry was added to 107 g of glycolonitrile in 330 ml ethanol at 5-10° C. over 3 hours. The addition of slurry of sodium salt of ethyl cyanoacetate to glycolonitrile resulted in clear solution with the liberation of heat. The solution was stirred at 5-10° C. for additional 1 hour and then raised the liquid temperature to 30° C. and equilibrated for 4 hours. The mixture was then cooled to 5-10° C. and neutralized to pH=4.45.

The reaction mass was further equilibrated for 1 hour. The mixture was filtered at 10° C. and washed the cake with ethanol. The filtrate and wash were combined and ethanol was distilled under vacuum, the crude 2,3-dicyano-ethyl propionate thus obtained was dissolved in dichloromethane and the solution was washed with cold water followed by 10% soda ash solution. The organic layer containing 2,3-dicyanoethyl propionate was dried over magnesium sulphate. The oily layer obtained after removal of dichloromethane was distilled under reduced pressure over a column to give ethyl-2,3-dicyanopropionate in 79.6% yield.

Example 11

Preparation of 5-aminopyrazole (VII)

To 2,6-dichloro-4-trifluoromethyl aniline 230 g and acetic acid 150 ml was added 1.1 m of nitrosyl sulphuric acid over one hour at 30° C. and maintained at 30° C. for one more hour. Heat the mass to 50-55° C. over ½ hour and the absence of 2,6-dichloro-4-trifluoromethyl aniline was monitored. Cool the mass to 30° C., and the excess nitrosyl sulphuric acid was destroyed.

The above diazotized mass was added to a mixture of 250 ml of acetic acid, 162 g ethyl-2,3-dicyanoproprionate and 425 ml water over 4-5 hours maintaining temperature 0-5° C. Further maintained at 0° C./2 hours, 5° C./1 hour, 10° C./1 hour, 15° C./1 hour. 800 ml water was added at 15° C. over ½ hour, extracted the solution with 3×250 ml methylene dichloride. Layers were separated. Dichloromethane layer was washed with 250 ml water, cooled the dichloromethane layer to 0° C. and washed with 250 ml 8N aq. NH3 under stirring for one hour. Layers were separated, dichloromethane layer was taken and NH3 gas was passed at 0-5° C. till free NH3 was observed on top of the condenser and maintained the reaction mass for 3-4 hours at 0-5° C. Then 250 ml water was added, stirred for ½ hour, layers were separated, extracted aq. layer with 2×100 ml dichloromethane, dichloromethane layer was dried with MgS04, dichloromethane layer was concentrated to dryness, to obtain 288 g of 5-amino-3-cyano-1-(2,6-dichloro-4-trifluoromethyl phenyl)-pyrazole of 98% purity.

Example 12

To a glass reactor having a central vertical stirrer, a vertical condenser & a dip tube for passing chlorine gas, was charged 730 ml of 3N HCl in 83.4 gm of carbon disulfide, 388 gm chlorine gas bubbled over 10 hrs at 24-25° C. Reaction was terminated when carbon disulfide was <1%. Trichloromethylsulfenyl chloride, 193 gm was obtained after work up & fractionation.

Trichloromethylsulfenyl chloride (193 gm) was added in to a mixture of 500 gm water & 100 ml methylene dichloride, along with 83 gm Sulfur dioxide gas at 10° C., over a period of 4 hrs. Reaction was terminated, when trichloromethyl sulfenyl chloride was <1%. Layer separation gave 228 g of thiophosgene which was added to a stirred mixture of 175 gm activated KF, 1 10 gm ortho-chlorobenzyl chloride and 340 gm spherogel (with 2 mm diameter), at 60° C., over a period of 3 hrs & further maintained at 60° C. for 2 hrs gave 98% conversion. ortho-Chlorobenzyl trifluoromethylsulfide (138 gms) was isolated by filtration, followed by distillation, which was added to 500 ml methylene chloride, cooled to 0 to 10° C. & 41 gm chlorine gas was bubbled into it, the reaction was maintained for 2 hrs & then heated slowly to 40-45° C. Generated trifluoromethylsulfenyl chloride was passed in to a solution of 5-amino-3-cyano-1-(2,6-dichloro-4-trifluoromethyl phenyl)-pyrazole in methylene dichloride to get 225 g of 5-amino-1-(2,6-dichloro-4-trifluoromethylphenyl)-3-cyano-4-trifluoromethyl thiopyrazole.

Example 13

In a mixture of 1200 gins of monobromoacetic acid, 300 gms of chlorobenzene, 2 gms of boric acid, was added 421 gms of 5-amino-1-(2,6-dichloro-4-trifluoromethylphenyl)-3-cyano-4-trifluoromethyl thiopyrazole and cooled to 15-20° C. Aqueous $H_2O_2$ (68 g, 50%) was added and mass was stirred for 20 hours. After work up 34% fipronil was isolated and 5-amino-1-(2,6-dichloro-4-trifluoromethylphenyl)-3-cyano-4-trifluoromethyl thiopyrazole from various streams was recycled. Fipronil thus obtained was purified using chlorobenzene to get 95% pure product.

Example 14

A mixture of 570 g of dibromoacetic acid and 30 gm tribromoacetic acid was taken along with 150 g of chlorobenzene, 1 g of boric acid and 211 g of 5-amino-1-(2,6-dichloro-4-trifluoromethylphenyl)-3-cyano-4-trifluoromethyl thiopyrazole. The mixture was cooled to 15-20° C.

Aqueous $H_2O_2$ (34 g, 50%) was added and mass was stirred for 23 hours. After work up 50% fipronil was isolated and 5-amino-1-(2,6-dichloro-4-trifluoromethylphenyl)-3-cyano-4-trifluoromethyl thiopyrazole from various streams was recycled. The Fipronil thus obtained was purified using chlorobenzene to get 96% pure product.

Example 15

A mixture of 120 g of tribromoacetic acid and 30 gm chlorobenzene, 0.2 g of boric acid and 42.1 g of 5-amino-1-(2,6-dichloro-4-trifluoromethylphenyl)-3-cyano-4-trifluoromethyl thiopyrazole was cooled to 20-25° C. Aqueous $H_2O_2$ (6.8 g, 50%) was added and mass was stirred for 23 hours. After work up 30% fipronil was isolated and 5-amino-1-(2,6-dichloro-4-trifluoromethylphenyl)-3-cyano-4-trifluoromethyl thiopyrazole from various streams was recycled. The Fipronil thus obtained was purified using chlorobenzene to get 95.7% pure product.

Example 16

A mixture of 86 g of dibromoacetic acid was taken along with 22 g of chlorobenzene, 0.15 g of boric acid and 30 g of 5-amino-1-(2,6-dichloro-4-trifluoromethylphenyl)-3-cyano-4-trifluoromethyl thiopyrazole. The mixture was cooled to 15-17° C. Aqueous $H_2O_2$ (4.84 g, 50%) was added and mass was stirred for 23 hours. After work up 55.5% of fipronil was isolated and 5-amino-1-(2,6-dichloro-4-trifluoromethylphenyl)-3-cyano-4-trifluoromethyl thiopyrazole from various streams was recycled.

Example 17

In to a mixture of 1200 gms of Trichloroacetic acid, 300 gms of chlorobenzene, 2 gms boric acid, added 5-amino-1-(2,6-dichloro-4-trifluoromethylphenyl)-3-cyano-4-trifluoromethyl thiopyrazole 421 gms and cooled the content to 15-20° C. Aqueous H₂0₂ (68 g, 50%) was added and mass was stirred for 20 hrs. After work up as above, 418 g of Fipronil of purity 94% was obtained. The filtered Fipronil was then purified using chlorobenzene (4 ml/g) followed by mixture (1 ml/g, 80:20 v/v) of Ethyl acetate and chlorobenzene to get 371 gms of Fipronil of greater than 97% purity. Example 18

A mixture of 700 g of dichloroacetic acid and trichloroacetic acid was taken along with 300 g of chlorobenzene, 2 g of boric acid and 280 g of 5-amino-1-(2,6-dichloro-4-trifluoromethylphenyl)-3-cyano-4-trifluoromethyl thiopyrazole, the content were cooled to 15-20° C. Aqueous H₂0₂ (44.2 g, 50%) was added and mass was stirred for 20 hrs. The mass was then processed and Fipronil was isolated by filtration. After work up as above, 269 g of Fipronil of purity 94% was obtained. The filtered Fipronil was then purified using chlorobenzene (5 ml/g) followed by mixture (1 ml/g, 80:20 v/v) of ethylacetate and chlorobenzene to get 232 g of Fipronil of greater than 97% purity.

Example 19

Purification of Fipronil

The fipronil prepared in example 18 of purity 97% was treated with a mixture (232 ml) of ethylacetate & chlorobenzene (80:20 v/v). This reaction mixture was heated to 85-90° C. & maintained for 1 hr. It was further cooled up to 30° C. in stages & filtered. Fipronil thus obtained had a purity of 98%. This cycle was repeated to obtain fipronil of above 98% purity.

The useful constituents from various streams of crystallization, leaching as above were reused and recycled, fipronil was isolated in 80-85% yield with purity of above 98%.

The numerical values of various parameters given in the specification are but approximations and slightly higher or slightly lower values of these parameters fall within the ambit and the scope of the present disclosure.

While considerable emphasis has been placed herein on the specific steps of the preferred process, it will be highly appreciated that many steps can be made and that many changes can be made in the preferred steps without departing from the principles of the present disclosure. These and other changes in the preferred steps of the present disclosure will be apparent to those skilled in the art from the disclosures herein, whereby it is to be distinctly understood that the foregoing descriptive matter is to be interpreted merely as illustrative of the present disclosure and not as a limitation.

The invention claimed is:
1. A process for the preparation of a trifluoromethylsulfinylpyrazole compound of formula I,

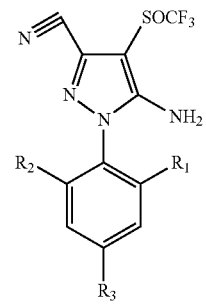

said process comprising:
a) halogenating an aromatic compound of formula II:

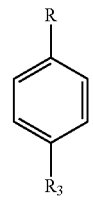

wherein, R is a halogen and $R_3$ is a perhaloalkyl, to obtain a polyhalogenated perhaloalkyl benzene compound of formula III;

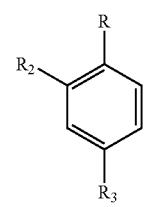

wherein, R and $R_2$ are halogen independently selected from the group consisting of F, Cl, Br, and I; and $R_3$ is a perhaloalkyl;
b) reacting in a polar solvent selected from the group consisting of N-methyl pyrrolidone, dimethylsulfone, N,N'-dimethyl imidazolidinone and diphenylsulfone; the compound of formula III with anhydrous ammonia in the presence of an alkali halide; at a temperature of about 200° C. to 300° C.; and a pressure of about 20 kg/cm² to about 50 kg/cm² to obtain a halo-perhaloalkyl aniline compound of formula IV,

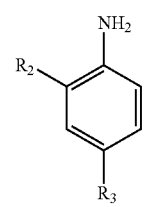

wherein $R_2$ is halogen and $R_3$ is a perhaloalkyl;
c) reacting halo-perhaloalkylaniline compound of formula IV with at least one halogenating agent selected from the group consisting of chlorine, sulfuryl chloride, thionyl chloride and phosphorus pentachloride, in a chlorinated solvent selected from the group consisting of chloroform, dichloroethane, dichloromethane, chlorobenzene and o-dichlorobenzene to obtain a product mixture containing polyhalogenated perhaloalkylaniline compound of formula V,

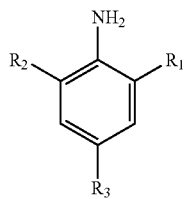

wherein, $R_1$ and $R_2$ are halogen independently selected from the group consisting of F, Cl, Br, and I; and $R_3$ is a perhaloalkyl;

d) isolating polyhalogenated perhaloalkylaniline compound of formula V from the product mixture;

e) diazotizing the isolated polyhalogenated aniline compound of formula V with nitrosyl sulfuric acid in the presence of an acid solvent to form a diazotized derivative of compound V;

f) reacting the diazotized derivative of compound V with cyanoalkyl propionate derivative and ammonia at a temperature range of about 0° C. to 25° C. to obtain a reacted mixture containing pyrazole compound of formula VII,

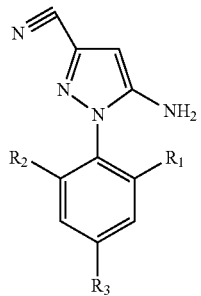

wherein, $R_1$ and $R_2$ are halogen independently selected from the group consisting of F, Cl, Br, and I; and $R_3$ is a perhaloalkyl;

g) isolating the pyrazole compound of formula VII from the reacted mixture with a halogenated aliphatic hydrocarbon solvent followed by evaporating the solvent to yield crude pyrazole compound VII;

h) sulfenylating the crude pyrazole compound VII with a sulfenylating agent in a halogenated aliphatic hydrocarbon solvent to obtain a product mixture containing thiopyrazole compound of formula IX,

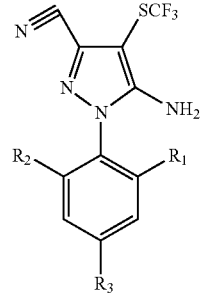

wherein, $R_1$ and $R_2$ are halogen independently selected from the group consisting of F, Cl, Br, and I; and $R_3$ is a perhaloalkyl; followed by isolating the thiopyrazole compound from the product mixture;

i) oxidizing the isolated thiopyrazole compound of formula IX at a temperature 10° C. to 30° C. in a reaction medium comprising an oxidizing agent which is a peroxide compound selected from the group consisting of hydrogen peroxide, tert-butyl hydrogen peroxide, benzoyl peroxide and sodium peroxide; a solvent system comprising in various ratios at least two solvents selected from a group of halogenated solvents consisting of trichloroacetic acid, di chloroacetic acid, mono bromoacetic acid, di bromoacetic acid, tri bromoacetic acid, chlorobenzene, dichloromethane and dichloroethane; and a corrosion inhibitor, to yield a product mixture containing trifluoromethyl sulfinyl pyrazole compound of formula I; and j) optionally purifying trifluoromethyl sulfinyl pyrazole compound of formula I by at least one process selected from the process consisting of crystallization which is carried out using at least one solvent selected from the group consisting of toluene, chlorobenzene and ethyl acetate; and leaching which is carried out using at least one solvent selected from the group consisting of toluene, chlorobenzene and ethyl acetate.

2. The process as claimed in claim 1, wherein R, $R_1$ and $R_2$ are chlorine and $R_3$ is trifluoromethyl.

3. The process as claimed in claim 1, wherein the solvent system in step (i) is a mixture of trichloroacetic acid, dichloroacetic acid and chlorobenzene.

4. The process as claimed in claim 3, wherein the chlorobenzene content in the mixture is about 20% to 30% w/w.

5. The process as claimed in claim 1, wherein the solvent system in step (i) is a mixture of trichloroacetic acid and chlorobenzene in a ratio of 80:20 w/w.

6. The process as claimed in claim 4, wherein the amount of the trichloroacetic acid is 5 to 14 molar equivalents.

7. The process as claimed in claim 1, wherein the amount of hydrogen peroxide used is about 0.5 moles to about 1.2 moles per mole of the compound of formula IX.

8. The process as claimed in claim 1, wherein the compound of formula II is 4-chlorobenzotriflouride.

9. The process as claimed in claim 1, wherein the compound of formula III is 3,4-dichlorobenzotriflouride.

10. The process as claimed in claim 1, wherein the compound of formula IV is 2-chloro-4-trifluoromethylaniline.

11. The process as claimed as claimed in claim 1, wherein the compound of formula V is 2,6-dichloro-4-trifluoromethylaniline.

12. The process as claimed in claim 1, wherein the cyanoalkyl propionate derivative is ethyl-2,3-dicyanopropionate.

13. The process as claimed in claim 1, wherein the compound of formula VII is 5-amino-3-cyano-1-(2,6-dichloro-4-trifluoromethyl phenyl)-pyrazole.

14. The process as claimed in claim 1, wherein the compound of formula IX is 5-amino-[2,6-dichloro-4-(trifluoromethyl)phenyl]-4-[trifluoromethyl sulfenyl]-1H-pyrazole-3-carbonitrile.

15. The process as claimed in claim 1, comprising step (j), wherein the chlorobenzene content in the mixture used for leaching ranges from 5% to 100% v/v.

16. The process as claimed in claim 1, wherein the chlorobenzene used for leaching is in the ratio of 2 to 10 parts per part of trifluoromethylsulfinyl pyrazole compound I.

17. The process as claimed in claim 1, wherein the purity of 5-amino-[2,6-dichloro-4-(trifluoromethyl)phenyl]-4-[-(1(R, S)-trifluoro methyl)sulfinyl]-1H-pyrazole-3-carbonitrile is greater than 98%.

* * * * *